United States Patent
Borch et al.

(10) Patent No.: US 6,955,538 B1
(45) Date of Patent: Oct. 18, 2005

(54) EQUIPMENT CONCERNING THE DEPOT OF MEDICAMENT IN THE MOUTH

(75) Inventors: Björn Borch, Tromsö (NO); John Thorleif Nilsson, Finnsnes (NO)

(73) Assignee: Decon AS, Tromso (NO)

( * ) Notice: Subject to any disclaimer, the term of this patent is extended or adjusted under 35 U.S.C. 154(b) by 0 days.

(21) Appl. No.: 10/258,603

(22) PCT Filed: May 5, 2000

(86) PCT No.: PCT/NO00/00151
§ 371 (c)(1),
(2), (4) Date: Nov. 5, 2002

(87) PCT Pub. No.: WO01/85056
PCT Pub. Date: Nov. 15, 2001

(51) Int. Cl.[7] .............................................. A61C 19/06
(52) U.S. Cl. ..................... 433/80; 433/229; 604/891.1; 424/435
(58) Field of Search ........................... 433/80, 81, 229; 604/891.1; 424/435

(56) References Cited

U.S. PATENT DOCUMENTS

| | | | | |
|---|---|---|---|---|
| 3,600,807 | A | * | 8/1971 | Sipos ......................... 433/167 |
| 4,671,768 | A | * | 6/1987 | Ton ............................. 433/174 |
| 4,764,377 | A | * | 8/1988 | Goodson .................... 424/435 |
| 4,959,052 | A | | 9/1990 | Cox |
| 5,090,903 | A | | 2/1992 | Taylor et al. |
| 5,197,882 | A | * | 3/1993 | Jernberg ..................... 433/215 |
| 5,503,558 | A | * | 4/1996 | Clokie ........................ 433/173 |
| 5,584,688 | A | * | 12/1996 | Sakuma et al. ............... 433/81 |
| 6,326,022 | B1 | * | 12/2001 | Katz .......................... 424/435 |

FOREIGN PATENT DOCUMENTS

EP        864299        9/1998

* cited by examiner

*Primary Examiner*—Ralph A. Lewis
(74) *Attorney, Agent, or Firm*—Dennison, Schultz, Dougherty & MacDonald

(57) ABSTRACT

A device for placing a slow-release supply in the oral cavity, typically in a tooth filling or dental prosthesis. The device includes a sleeve having an opening at least at one end and adapted to be inserted in a recess of the filling or prosthesis, and which is substantially cylindrical in shape. At the end which is to be place deepest within the filling or prosthesis, the sleeve has a diameter which is somewhat larger than the remainder of the sleeve in order to form a groove.

8 Claims, 1 Drawing Sheet

EQUIPMENT CONCERNING THE DEPOT OF MEDICAMENT IN THE MOUTH

BACKGROUND OF THE INVENTION

The present invention relates to a method designed to place a slow-release supply of a substance in the oral cavity and a device designed to implement said method. The slow-release supply can contain one or several medicaments or a sacrificial anode in the case of oral galvanism.

In human beings, the required medication is usually administered orally or rectally. When a regular slow release of medicaments for a certain period of time is necessary, a slow-release device is placed under the skin. The placing of such slow-release devices involves minor surgery.

Oral medication is effected either by swallowing or, in the case of tablets, by sucking the tablet so that its contents dissolves and is absorbed in the blood stream through the mucous membrane in the mouth. Pills are dissolved by the saliva which is always present in the mouth. The thinness of the skin and of the mucous membrane allows the medication to be readily diffused in the blood. The quantity of medication which is diffused in the oral cavity, swallowed or administered rectally is always small.

For dental treatment and in the case of infection or inflammation of the tooth canals and roots, it is common to place slow-release analgesic medication in a root canal and to seal the canal temporarily. The placing of such slow-release medication can require anaesthesia of the area which is going to be worked on and is also done in connection to the extensive work involved in repairing a damaged tooth. In addition, slow-release medication for the treatment of a local area are placed in the tooth concerned or in its vicinity.

The methods used by doctors or by dentists for placing slow-release medication requires surgery and anaesthesia of the patient. Placing slow-release devices for medication of the entire body require at least minor surgery under the skin.

SUMMARY OF THE INVENTION

The object of the present invention is to provide a method and device for placing the slow-release medication in the oral cavity in such a manner that later replacement of the slow-release device will not require surgery involving anaesthesia. A further object of the invention is to avoid discomfort for the patient.

This is achieved by providing, from the surface of a tooth filling, a recess in such filling in which a device containing the medication is placed, the recess remaining open to the surface.

BRIEF DESCRIPTION OF THE DRAWINGS

Further details of the invention appear from the following description of a preferred embodiment of the invention with reference to the illustrations.

DESCRIPTION OF THE PREFERRED EMBODIMENTS

Figure 1:
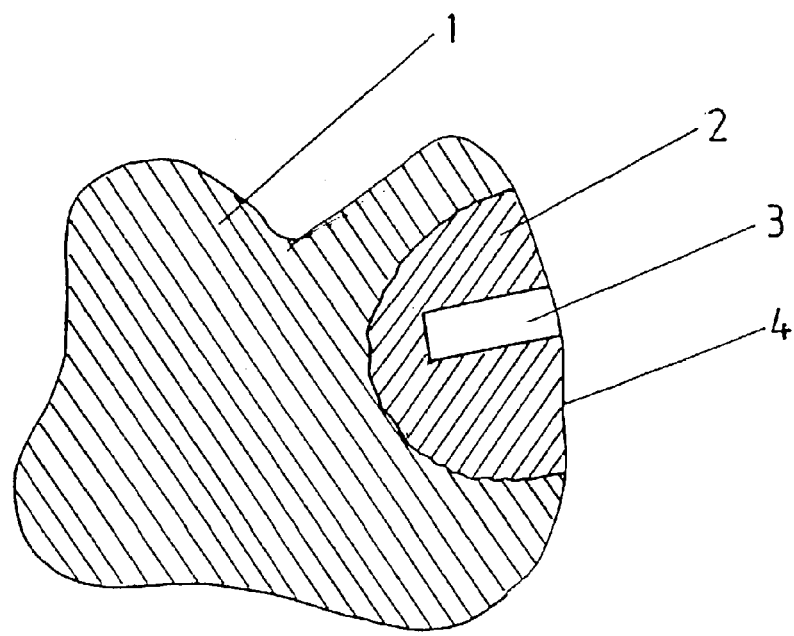
FIG. 1 shows a tooth filling with an insert for placing slow-release medication.
Figure 2:
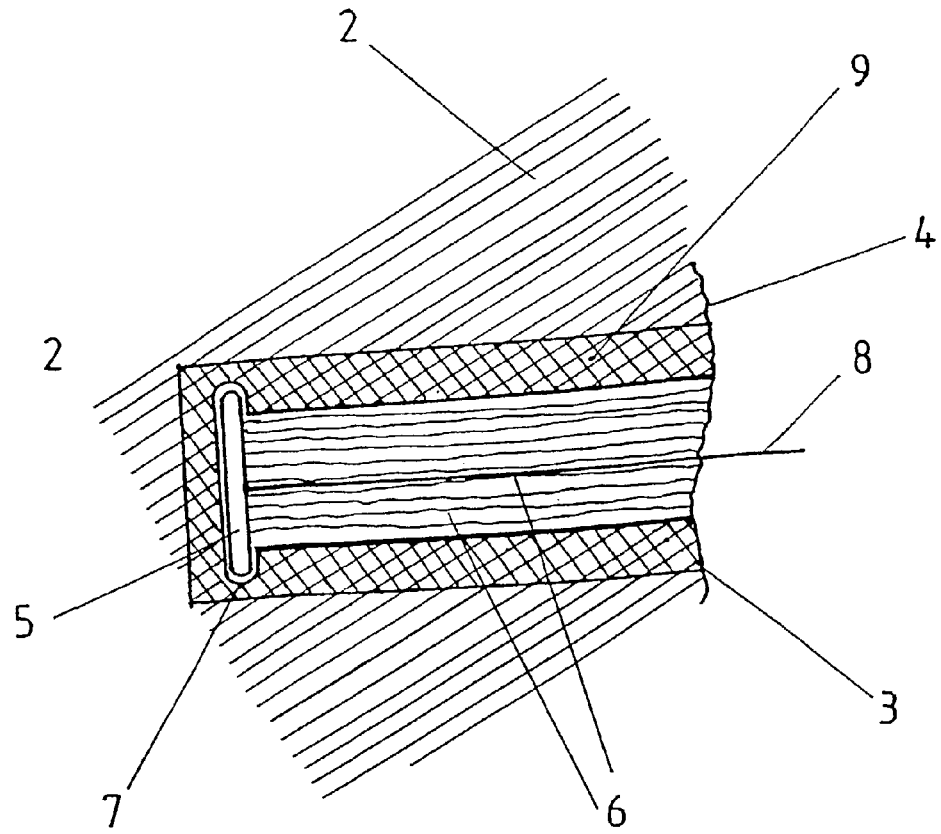
FIG. 2 illustrates the device containing the slow-release medication which is placed inside the tooth filling.

FIG. 1 is a cross section of a tooth 1 with a filling 2. This is assumed to be a filling 2 in the tooth 1 as a result of repairing a tooth cavity. The filling 2 can be a plastic or a porcelain filling, or be made of any other known filling material commonly in use for dental treatment. In this filling 2, an adequate recess 3 is drilled from the surface 4 of the filling 2. In the recess 3, a sleeve 9 is placed, around which fling material is packed so as to hold it firmly in place. In the sleeve 9, a device is inserted containing slow-release supply. This slow-release supply can itself contain medication or a material which may function as a sacrificial anode to alleviate oral galvanism. An embodiment of such a device for slow release in place in the recess 3 is illustrated in FIG. 2.

The slow-release device consists of a base 5 which can be shaped like a plate or like a circular ring inside which medication in liquid form can be placed. A large number of fibers 6 are attached to the base 5 and end at the level of the surface 4 of the filling 2. These fibers 6 may be made of a material permitting them to be hollow and to contain the medication, or of a material enabling them to draw the medication out of a quantity stocked in the base 5. The fibers 6 can also be designed in a material which has the ability to hold the medication on its surface and to release it a little at a time. In other words, the stock of medication can be placed either in the base 5 itself, or be absorbed by the fibers 6 and released to the surface 4 and further into the saliva and oral cavity, or the slow-release medication is placed in the fibers 6 themselves and is absorbed directly from those.

The base 5 can act as a mounting plate for the fibers 6, as storage place for the medication and as a fixing element for the device in the recess 3. The base 5 may be designed with a diameter somewhat larger than the recess 3 and the bottom of the recess 3 itself designed with a groove 7 where the base 5 may be snapped into place and stay put. There can be several methods for inserting the whole base 5 complete with the fibers 6 in the recess 3 and secure them in the groove 7. A grip 8 designed as a thin rod which is secured to the base 5 and is slightly longer than the fibers 6 can be used to insert the device and its base 5 in the recess 3 until it snaps into place in the groove 7. The grip 8 can subsequently be broken off just below the surface 4, between the fibers 6. When it is time to remove the device which has dried out, the dentist or the patient may use tweezers or any other appropriate tool to get hold of the remains of the grip 8 and pull the device out.

An important aspect of this system is that there must be a sufficient quantity of fibers 6 to prevent the recess 3 from filling with food remains.

The recess 3 can be provided in an existing filling, which most people have in one or several teeth already, or in dental prostheses before mounting these in the patient's mouth.

Furthermore, medication of various types can be placed in these slow-release devices. In addition to slow-release medication for dental treatment, medication for treatment and prevention destined to the whole body can also be used as the medication is drawn out to the oral cavity and to the saliva and is, from there, absorbed into the blood stream.

For a preferred embodiment of the slow-release device, fibres have been chosen to retain the medication and to release it over a period of time. There will be other materials which can, as required, have the same function, such as porous materials, a cluster of small spheres or sintered materials.

What is claimed is:

1. A device for depositing a slow release supply of an active substance in the oral cavity, comprising:
    a substantially cylindrical sleeve constructed and arranged for receipt in a filling of a tooth or in a dental prosthesis, said sleeve having a recess with a predetermined diameter extending from an open first end to a closed opposite end;

a base constructed and arranged to be retained within the recess of the sleeve at the closed end; and a delivery medium for active substance secured to the base and extending within the recess toward the open end, said delivery medium preventing ingress of food particles in the recess;

wherein at least one of the base and the delivery medium is adapted to receive and store a slow release supply of the active substance, and the delivery medium is adapted to deliver the slow release supply of the active substance to the open end of the recess in a time controlled manner.

2. The device of claim 1, wherein the delivery medium comprises fibers secured at one end thereof to the base.

3. The device of claim 1, wherein the closed end of the recess is in the form of a groove of greater diameter than an adjacent recess portion, and the base is retained in the groove.

4. The device of claim 1, wherein the base comprises a hollow plate or ring which contains the active substance.

5. The device of claim 4, wherein hollow ring contains a compartment for the active substance.

6. The device of claim 1, wherein one of the base and the delivery medium contains a material which functions as a sacrificial anode against effect of oral galvanism.

7. The device of claim 1, wherein a plurality of active substances is contained within at least one of the base and the delivery medium.

8. The device of claim 1, additionally comprising a gripping means secured to the base and extending at least to the open end.

* * * * *